United States Patent
Bergfjord et al.

(10) Patent No.: US 9,522,286 B2
(45) Date of Patent: Dec. 20, 2016

(54) RADIOTHERAPY APPARATUS

(71) Applicant: Elekta AB (Publ), Stockholm (SE)

(72) Inventors: Per Harald Bergfjord, West Sussex (GB); Francesco Gnoato, Tombolo (IT)

(73) Assignee: ELEKTA AB (PUBL), Stockholm (SE)

( * ) Notice: Subject to any disclaimer, the term of this patent is extended or adjusted under 35 U.S.C. 154(b) by 0 days.

(21) Appl. No.: 14/524,605

(22) Filed: Oct. 27, 2014

(65) Prior Publication Data

US 2015/0144811 A1    May 28, 2015

(30) Foreign Application Priority Data

Oct. 28, 2013 (GB) .................................. 1318983.2

(51) Int. Cl.
*A61N 5/01* (2006.01)
*A61N 5/10* (2006.01)

(52) U.S. Cl.
CPC .............. *A61N 5/01* (2013.01); *A61N 5/1081* (2013.01); *A61N 2005/1057* (2013.01)

(58) Field of Classification Search
CPC ................... A61N 2005/1057; A61N 5/1081; A61N 5/01
See application file for complete search history.

(56) References Cited

U.S. PATENT DOCUMENTS

| | | | |
|---|---|---|---|
| 2,781,454 A | 11/1953 | Green et al. | |
| 4,628,523 A * | 12/1986 | Heflin | A61N 5/10 250/522.1 |
| 5,799,054 A * | 8/1998 | Hum et al. | 378/17 |
| 6,969,194 B1 * | 11/2005 | Nafstadius | 378/197 |
| 7,188,999 B2 * | 3/2007 | Mihara et al. | 378/197 |
| 8,629,415 B2 * | 1/2014 | Fadler | A61B 6/0407 250/491.1 |
| 8,662,757 B2 * | 3/2014 | Zhang | A61B 6/03 384/549 |
| 2002/0015470 A1 * | 2/2002 | Tybinkowski et al. | 378/17 |
| 2002/0168044 A1 * | 11/2002 | Tybinkowski | A61B 6/4447 378/4 |
| 2006/0215813 A1 * | 9/2006 | Scherch et al. | 378/65 |
| 2007/0023699 A1 * | 2/2007 | Yamashita | A61N 5/10 250/492.21 |
| 2007/0029510 A1 * | 2/2007 | Hermann et al. | 250/493.1 |

(Continued)

FOREIGN PATENT DOCUMENTS

EP    0 203 647 A2    12/1986
EP    1 738 798    1/2007

(Continued)

OTHER PUBLICATIONS

GB Search Report, issued in corresponding Application No. GB 1318983.2, dated May 27, 2014, one (1) page.

(Continued)

*Primary Examiner* — Michael Logie
(74) *Attorney, Agent, or Firm* — Finnegan, Henderson, Farabow, Garrett & Dunner, LLP (57) ABSTRACT

A radiotherapy apparatus includes a rotatable drum on which is mounted a gantry arm carrying a radiation source, the arm extending from the drum to locate the source is offset from the axis of rotation of the drum and oriented towards the axis, and a mechanism to apply a tilt to the arm depending on the rotational orientation of the drum.

7 Claims, 5 Drawing Sheets

(56) References Cited

U.S. PATENT DOCUMENTS

2009/0139344 A1* 6/2009 Lindeman ............... G01N 3/04
                                                        73/859
2010/0163755 A1* 7/2010 Takeda et al. ............. 250/492.3
2012/0035470 A1* 2/2012 Kuduvalli ................ A61B 6/00
                                                        600/427
2014/0023175 A1* 1/2014 Yamaguchi ...................... 378/4
2014/0121442 A1* 5/2014 Matteo et al. ................... 600/1

FOREIGN PATENT DOCUMENTS

GB          2245539 A  *  1/1992  ............... B66F 3/20
WO    WO 2013-093020      6/2013

OTHER PUBLICATIONS

Extended European Search Report, issued in related Application No. EP 14183211, dated Mar. 4, 2015, 6 pages.

* cited by examiner

RADIOTHERAPY APPARATUS

CROSS REFERENCE TO RELATED APPLICATION

The present application claims the benefits of priority to U.K. Patent Application GB 1318983.2, filed Oct. 28, 2013, the entire content of which is incorporated herein by reference.

FIELD OF THE INVENTION

The present invention relates to radiotherapy apparatus.

BACKGROUND ART

Many designs of radiotherapy apparatus employ a radiation source mounted on a gantry arm that is rotatable around a patient support on which a patient can be placed for treatment. The usual geometry for this is to provide a circular-section rotatable drum oriented in a vertical plane, i.e. with its axis of symmetry and rotation in a horizontal plane, and mount the gantry arm onto the drum, offset from the axis. The source is then mounted at the end of the gantry arm, oriented so that the beam that it produces is directed towards the axis. The point at which the centre of the beam meets the axis is known as the "isocentre". Thus, as the drum rotates, the beam arrives at the isocentre from all angular directions within a vertical plane. This is an important aspect of the radiotherapy treatment, as it allows a sufficient dose to be delivered to a target volume while minimising the dose delivered to surrounding healthy tissue.

Usually, the rotating drum is supported on four main wheels beneath the drum, arranged in two angularly-offset pairs, one pair at a front edge of the drum and one pair at a rear edge. The drum and the gantry arm are usually substantial items in order to support the weight of the radiation source mounted in the arm and at the end thereof. Despite this, there will be some small degree of flexure in the gantry arm, resulting in a "droop' effect, i.e. an unintended movement of the isocentre. With the gantry at the top of the drum (defined as 0° of rotation) the movement of the isocentre Is along the axis towards the drum, whereas at 180° rotation with the gantry at the bottom of the drum, the movement of the isocentre is along the axis away from the drum. Whilst this is known, measurable effect that can be planned and compensated for during treatment, it would be additionally beneficial to minimize the effect where possible.

SUMMARY OF THE INVENTION

If this movement could be reduced, then the accuracy of delivery of the radiation dose could be improved. Hitherto, this has been seen as a mechanical problem to be solved by stiffening the drum and the gantry arm, but this usually results in an increase in the weight of the moving parts.

We propose a different approach, according to which a variable tilt is applied to the gantry depending on its rotational orientation. This tilt can act in opposition to the droop and return the radiation source to its correct location and orientation.

This tilt could be achieved in one of a number of ways. A mechanical actuator within the drum or beneath the wheels on which it rotates could be driven in response to a rotation sensor in order to tilt the gantry and/or the drum. The drum itself could be made non-circular in at least some of the areas that are supported by the wheels, so that the rotation is not completely smooth but causes the drum to tilt as it rotates. Alternatively, the wheels can be arranged to lift and/or lower as the drum rotates.

A mechanism within the wheels could use an eccentric mechanism in order to adjust the position of the wheels as they rotate. Generally, the wheels will have a much smaller radius than that of the drum, so to synchronise the movement of the wheels with the rotation of the drum, a gearing arrangement such as an epicyclic gear can be employed. The epicyclic gear can include the eccentric mounting.

An epicyclic gear arrangement essentially comprises a sun wheel, a planetary gear, and an annulus, and in this implementation the SLJn wheel can be fixedly attached to a bearing surface of the wheel, the planetary gear mounted eccentrically on a supporting base, and the annulus held in a non-rotating relationship with the supporting base.

A further possibility is to make non-circular at least one of the circumferential bearing surface or surfaces by which the rotating drum is supported on wheels.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
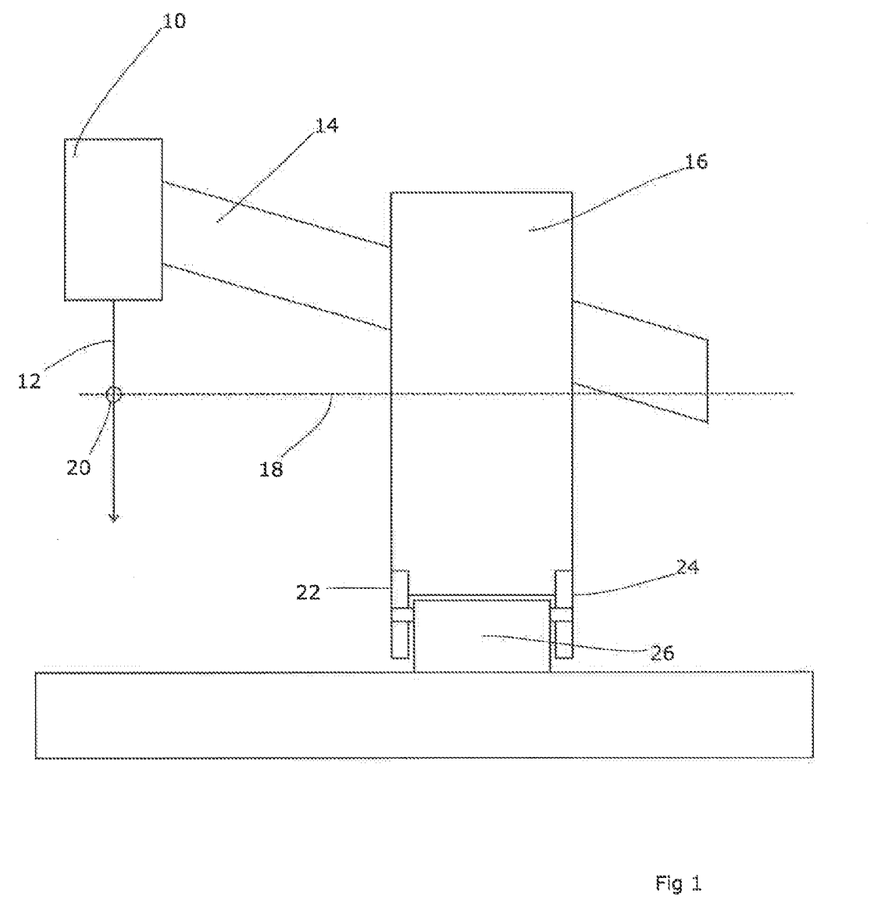
FIG. 1 shows a vertical cross-section through a radiotherapy apparatus, shown in schematic form.

Referring to FIG. 1, a radiotherapy apparatus comprises a radiation source 10 which emits a beam of radiation along a beam axis 12. The source 10 is mounted on a gantry arm 14 which is itself supported by a rotatable drum 16. The drum is arranged vertically, i.e. with its axis 18 of rotational symmetry substantially horizontal, and is able to rotate about that axis 18 carrying with it the gantry arm 14 and the source 10. An electrical drive motor is provided (not shown) in order to drive rotation of the drum 16 when required, and in the direction required. The arm 14 is mounted to the drum 16 so as to support the source 10 at a location offset from the rotation axis 18 but pointing towards the rotation axis 18. The location 20 at the meeting point of the beam axis 12 and the rotation axis 18 is referred to as the "isocentre" 20. Thus, as the drum 16 rotates, the source rotates around the isocentre, directing a beam toward that isocentre continuously. This is useful during treatment, as a dose can be applied to a target volume located at the isocentre with only a brief or limited irradiation of the surrounding tissue.

The drum 16 is supported during its rotation by wheels. These are arranged (in this example) as a set of four wheels, two wheels 22 supporting a front edge of the drum 16 and two wheels 24 supporting a rear edge of the drum 16. The wheels in each pair are located either side of the lowest point of the drum 16, thus defining a rectangular pattern and supporting the drum 16. The wheels are mounted on a suitably rigid base 26, usually able to freewheel (although see later for certain embodiments).

FIGS. 2a-2d show how the position of the gantry 14 and the source 10 can be adjusted by way of an adjustment of the supporting wheels. Both the gantry and the source are of course subject to the influence of gravity, and thus as the source 10 rotates, gravity will cause elastic deformation of the gantry 14 due to the substantial weight of the source 10. FIGS. 2a-2d show how a raising and lowering action on the supporting wheels can be used to provide a correction to the isocentre position; in each case in FIGS. 2b and 2d the correction operates by moving the apparatus from the position shown in solid lines to the position shown in dotted lines.

Figure 2A:
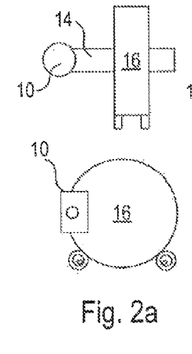
FIGS. 2a, 2b, 2c, and 2d show the adjustments needed to the gantry arm in order to correct for droop.

FIGS. 2a and 2e show the source at the 270° and 90° positions respectively. Some deformation of the gantry arm 14 is apparent at these angles, generally having the effect of lowering the beam isocentre towards the ground. The effect of this is not as great as the deformation at the 0° and 180° positions, so at this stage the embodiments focus on ameliorating the latter. The 90° and 270° deformations may benefit from similar treatment in future.

Figure 2B:
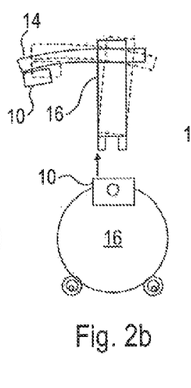
Figures 2C, 2D:
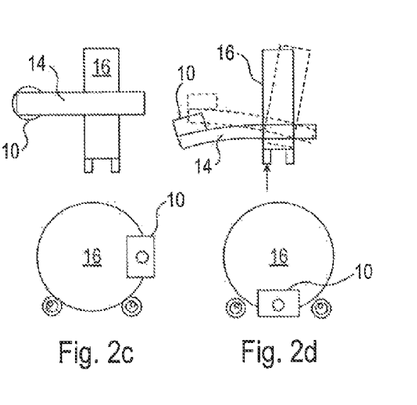

FIG. 2b shows the source in the 0° position, i.e. at its highest point and directed substantially vertically downwards. In this position, an elastic deformation of the gantry arm 14 will tend to cause the source 10 to "droop', resulting in the source 10 pointing slightly towards the drum 16 (the droop is exaggerated for clarity). This adjustment of the beam axis 12 tends to draw the isocentre towards the drum 16 slightly. This can be counteracted by slightly raising the front wheels as shown in FIG. 2(b) (or by lowering the rear wheels), leaning the entire apparatus out away from the drum position shown in the solid line to that shown in the dotted line and moving the isocentre outward.

Conversely, with the source at the 180° position as shown in FIG. 2d, the elastic deformation of the gantry arm 14 tends to tilt the source 10 outwards so that the beam axis is slightly divergent away from the drum 16. This therefore moves the isocentre slightly away from the drum 16, and can be counteracted by slightly raising the front wheels as shown (or by lowering the rear wheels) in order to angle the beam more towards the drum.

Thus, one way of correcting for the droop effect, according to a first embodiment of the present invention, is to adjust the position of the drum 16 via the wheels 22, 24. An upward adjustment of the front wheels 22, or a downward adjustment of the rear wheels 24, will tend to adjust the isocentre position away from the drum 16, and vice versa (i.e. lowering the front wheels or raising the rear wheels adjusts the isocentre position towards the drum). Thus, this can be used to fine-tune the isocentre position and counteract the influence of gravity.

Figure 3:
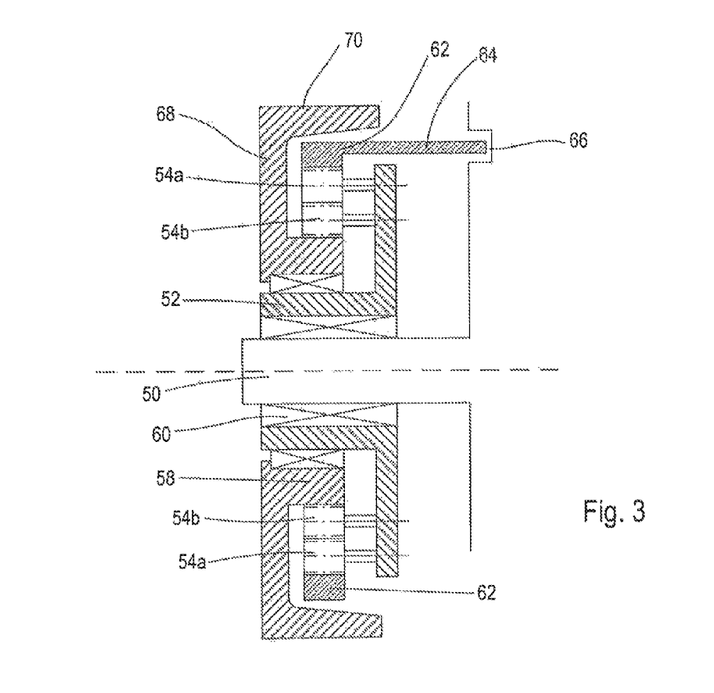
FIGS. 3 and 4 show side and front views respectively of an epicyclic gear arrangement for a supporting wheel for use in the present invention, FIG. 4 in schematic form.
Figure 4:
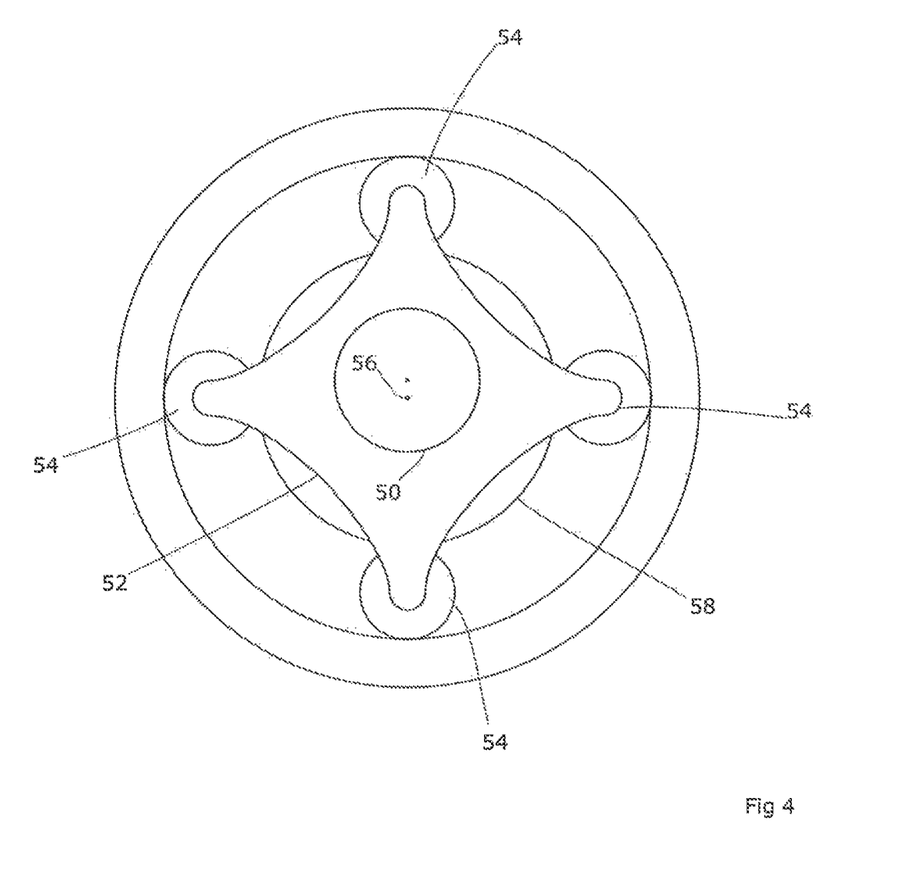

The heights of the wheels 22, 24 could be adjusted via a cam surface within the wheel mountings, for example, or by any suitable mechanism. Our preferred mechanism is shown in FIGS. 3 and 4 and comprises an epicyclic gear train within the wheel itself. FIG. 3 shows the gear train in section, mounted on a rigid stub axle 50. A planetary gear carrier 52 is mounted eccentrically on the stub axle 50 and carries a set of four planetary gears 54, each spaced equally from the eccentric centre 56 of the planetary gear carrier 52. More planetary gears 54 could be provided, such as 5 or 6, to give a smoother action. Alternatively, fewer gears such as 2 or 3 could be provided to reduce the weight and complexity of the device. The choice may also be influenced by the gear ratio, as a smaller planet gear set may allow for and benefit from a larger number of gear wheels. The planetary gears 54 engage with a sun wheel 58 located radially within the planetary gears 54 and journalled to rotate freely around the planetary gear carrier 52 on a set of bearings 60. An annular ring gear 62 is provided around and engaging with the planetary gears 54; this is prevented from rotation by engagement of a pin 64 in a slot 66 formed in the base on which the stub axle 50 is provided.

The sun gear 58 includes a flange section with two sections, a first section 68 that extends radially outwardly, spaced axially away from the planetary gears 54, the planetary gear carrier 52, and the annular ring gear 62, and a second section 70 that extends axially away from an outer end of the first section 68 to provide a circumferential cover around the epicyclic gear arrangement. The circumferential outer face of the recon section 70 defines the outer bearing face of the wheel.

Thus, as the drum 16 rotates ill drive the wheel via the outer face of the second section 70, and hence drive the sun gear 58. This, in turn, will drive the planetary gears 54 around within the annulus 62. As the planetary gear carrier 52 moves, its eccentric mounting on the stub axle 50 will cause it to oscillate, carrying with it the sun gear and hence the wheel bearing surface. The annular ring gear 62 will also oscillate, but will be confined to a back and forth linear motion by the engagement of the pin 64 in the slot 66. The rate of the oscillation will depend on the gear ratio of the epicyclic, which can therefore be chosen to reflect the ratio of the drum radius to the wheel radius.

By choosing an appropriate gear ratio, the wheel can be made to complete one complete oscillation with one complete rotation of the drum 16. It should be noted that FIGS. 3 and 4 are not to scale and (for the purposes of clarity) do not illustrate a suitable gear ratio. Thus, at the 0° position of the drum, the rear wheels 24 can be aligned so as to lift the drum slightly and correct the droop of the gantry arm 14. The degree of lift is of course determined by the degree of eccentricity of the planetary gear carrier 52 around the stub axle 50. Likewise, with the gantry at the 180° position, the rear wheels will have completed half an oscillation (relative to the 0° position) and will be at their lowest point, thus counteracting the opposite droop of the gantry arm 14 at that point. The vertical motion of the wheel is sinusoidal, which matches the movement of the isocentre which is also sinusoidal due to the action of gravity on the cantilevered beam arm as it rotates.

It is also possible to raise/lower the front wheels, but it is better to keep the pivot as far forward as possible as this gives more horizontal movement of the isocentre from a specific vertical movement of the wheels. It is therefore best to raise/lower the rear wheels. In practice, the space envelope around the rear wheels is also greater, giving more room for the mechanism.

As can be seen in FIGS. 2a-2d, the hub of each of the rear wheels rotates in opposite directions. This is to stabilise the drum by preventing sideways translation of the gantry as it rotates. To achieve this, one wheel should be as described above and illustrated in FIG. 4, while the other should be as illustrated in FIG. 3 with each planetary gear 54 being a reversing gear, such as being made of two smaller gears engaging with each other, one of which engages with the sun gear 58 and one engaging with the annular ring gear 62.

As noted above, the annular gear 62 is held in a non-rotating relationship with the base. This can be by way of a pin or blade extending from the annulus into a radially-arranged slot in the base (or vice-versa).

The gantry wheel may drift over time relative to the drum, due to the drum skidding over the wheel. Thus, an indexing device will be preferred. This could be in the form of a feature on the drum engaging with the wheel at regular intervals, such as a gear or tooth, or by way of a high-friction surface on one or both of the wheel and drum, or the like.

An alternative solution, according to a second embodiment of the present invention, is to adjust the mounting of the gantry arm 14 within the drum 16. As only a very small adjustment is needed, and the load transmitted from the arm to the drum is large, we expect this to be difficult but achievable through the use of levered cam surfaces driven by suitable actuators.

Figure 5:
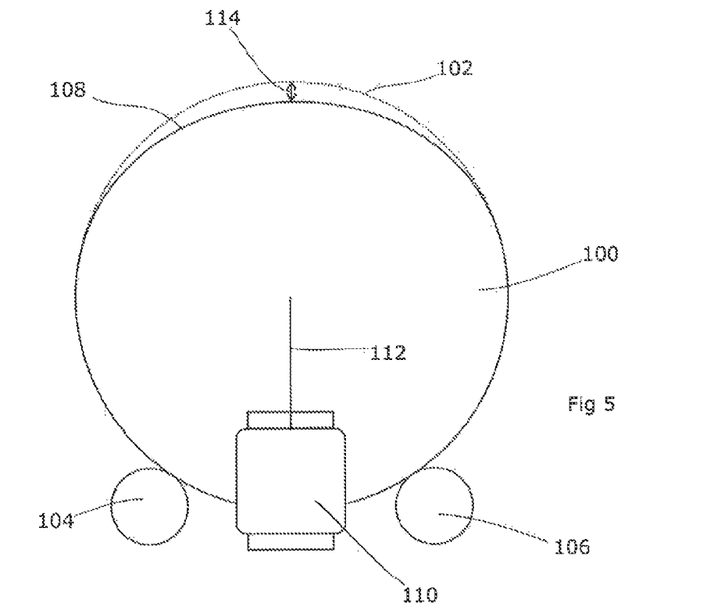
FIGS. 5 and 6 show a third embodiment of the present invention.
Figure 6:
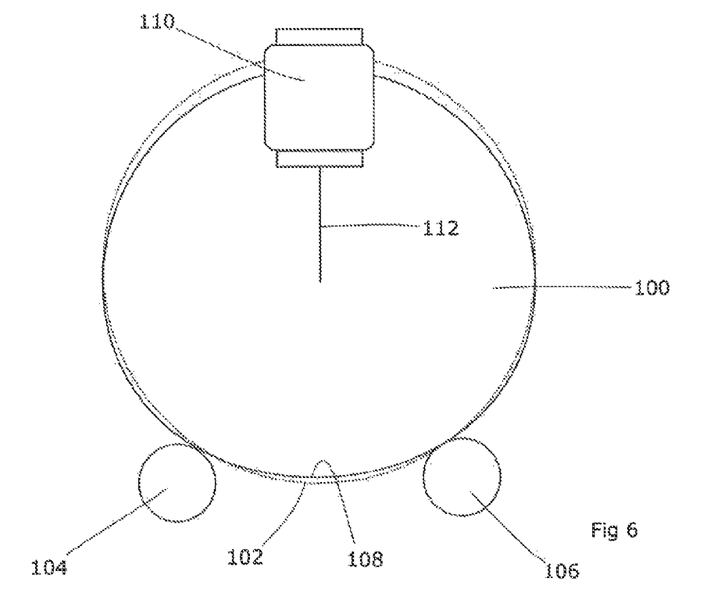

FIGS. 5 and 6 show a third embodiment in schematic form, illustrated from the front of the apparatus and along the axis of rotation of the drum. Thus, the drum 100 is supported in the manner shown in FIG. 1 by a set of four wheels. Two rear wheels (not shown) support a rear rim 102 of the drum 100, and two front wheels 104, 106 support a front rim 108 of the drum 100. A radiation source 110 is mounted on the drum via a gantry and emits a beam 112 towards the rotation axis of the drum 100.

The drum thus carries the two rims via which it is supported, the rear rim 102 and the front rim 108. These will usually be defined by a suitable rigid bearing surface along which the wheels 104, 106, etc. roll. The rear rim 102 is (in this embodiment) circular, centred on the rotation axis of the drum 100 and thus rotationally symmetric around that axis. However, the front rim 108 is slightly non-circular, having a smooth indentation 140 compared to the circular rear rim 102 (shown in dotted lines). Otherwise, the front rim 108 is circular. This indentation 114 is located opposite the radiation source 110, so when the source 110 is at the 0° position (FIG. 6) the front rim of the drum 100 will be allowed to rest slightly lower than the rear rim 102. This will therefore tilt the drum slightly toward the isocentre in the manner of FIG. 2*b*, correcting the droop of the gantry arm under gravity. With the source 100 at the 1800 position, the front rim 108 (of this embodiment) is being supported at a circular portion thereof.

This means that at the 180° position, the drum is at its "default" position. That default position (and that of the wheels, gantry and source) can be adjusted so that the appropriate gravity compensation is made at the 180° position, and then reversed by the indentation 114 at the 0° position. Alternatively, the absence of compensation at the 1800 position can simply be accepted. In another alternative, the front rim 108 can be given a protrusion opposite the indentation 114, to tilt the drum 100 in the opposite direction at the 180° position. Indeed, the indentation 114 on the front rim 108 could be replaced with a protrusion on the rear rim 102. In a further alternative, the rear rim 102 can be given an indentation opposite that of the front rim 108. Of course, the various alternatives could be combined, with some degree of indentation or protrusion on both rims so as to secure the desired tilt at all points of the rotation of the drum 100.

Figure 7:
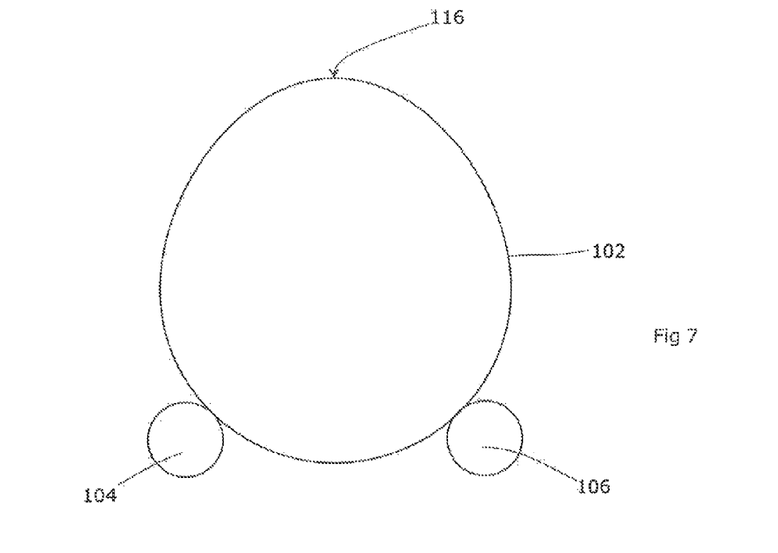
FIG. 7 shows a fourth embodiment of the present invention.

FIG. 7 schematically illustrates a version of the rear rim 102 with such a protrusion 116.

Figure 8:
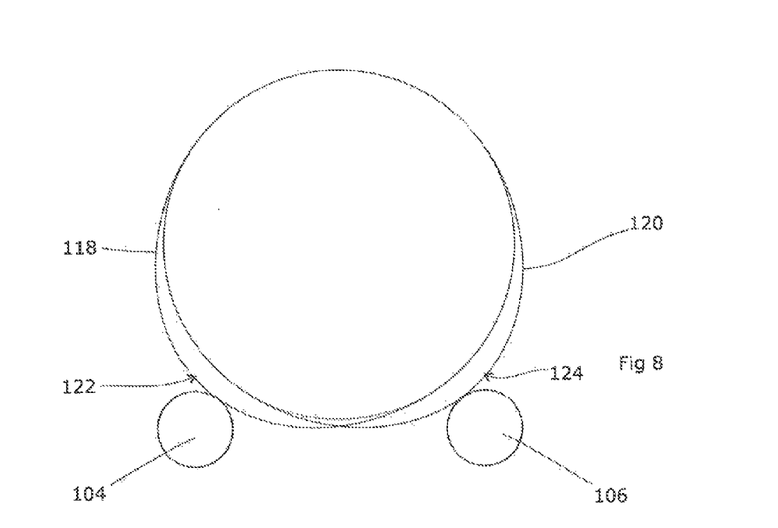
FIG. 8 shows a fifth embodiment of the present invention.

FIG. 8 schematically illustrates a fifth embodiment which offers the potential for greater control of the drum orientation at a wider range of angles. It entails splitting the front (and/or rear) rim into two sub-rims 118, 120 and offsetting the two wheels 104, 106 that support the rim so that the wheel 104 on one side supports one sub-rim 118 and the wheel 106 on the other side supports the sub-rim 120. We prefer that the two sub-rims are adjacent, although they may have an upstanding ridge between them in order to prevent a wheel slipping onto the wrong rim. In this example, the two sub-rims 118, 120 each have a protrusion 122, 124 respectively, spaced 90° apart. Thus, at one position of the drum both protrusions 122, 124 meet the wheels and a maximum lift is obtained. This design flexibility could be used in order to tailor the precise orientation of the drum, offering many degrees of freedom given the four wheels supporting the drum and the ability to engineer protrusions and indentations around the circumference of (potentially) four corresponding sub-rims. This could be used to compensate for gravity-induced droop at all rotational positions.

It will be appreciated that in all of FIGS. 5 to 8, the various deviations from circularity are grossly exaggerated in order to render them visible. In practice, the deviations are likely to be of a sub-millimeter order.

It will of course be understood that many variations may be made to the above-described embodiment without departing from the scope of the present invention.

The invention claimed is:

1. A radiotherapy apparatus, comprising:
a rotatable drum on which is mounted a gantry arm carrying a radiation source, wherein the arm extending from the drum to locate the source is offset from the axis of rotation of the drum and oriented towards the axis, wherein the drum has two edges along the axis of rotation including a front edge near the arm and a rear edge away from the arm; and
a cam mechanism configured to apply a variable tilt to the arm at one or more rotational orientations of the drum, wherein the cam mechanism is configured to adjust at least the rear edge of the drum such that the rear edge of the drum is at a different height to the front edge of the drum, wherein the cam mechanism varies the tilt according to the rotational orientation of the drum,
wherein the rotating drum is supported on wheels beneath the drum, and the mechanism is an eccentric mechanism within the wheels and applies the tilt to the drum via the wheels.

2. The radiotherapy apparatus according to claim 1, wherein the mechanism applies the tilt to the drum and thereby tilts the arm away from the drum.

3. The radiotherapy apparatus according to claim 2, further comprising at least four wheels arranged in two angularly-offset pairs, one pair is located at the front edge of the drum and one other pair is located at the rear edge of the drum.

4. The radiotherapy apparatus according to claim 3, further comprising a mechanical actuator within the drum or beneath the wheels on which it rotates, the mechanical actuator being configured to be driven in order to tilt the arm and/or the drum in response to a rotation sensor.

5. The radiotherapy apparatus according to claim 1, wherein the rotating drum is supported on wheels which contact circumferential bearing surfaces on the drum, and wherein at least one circumferential bearing surface is non-circular.

6. A radiotherapy apparatus, comprising:
a rotatable drum on which is mounted a gantry arm carrying a radiation source, wherein the arm extending from the drum to locate the source is offset from the axis of rotation of the drum and oriented towards the axis, wherein the drum has two edges along the axis of rotation including a front edge near the arm and a rear edge away from the arm; and
a cam mechanism configured to apply a variable tilt to the arm at one or more rotational orientations of the drum, wherein the cam mechanism is configured to adjust at least the rear edge of the drum such that the rear edge of the drum is at a different height to the front edge of the drum, wherein the cam mechanism varies the tilt according to the rotational orientation of the drum, wherein the rotating drum is supported on wheels beneath the drum and the mechanism applies the tilt to the drum via the wheels, the mechanism is contained within the wheels, and the mechanism is an epicyclic gear arrangement including an eccentric mounting.

7. The radiotherapy apparatus according to claim 6, wherein the epicyclic gear arrangement comprises a sun wheel, a planetary gear, and an annulus, and wherein the sun wheel is fixedly attached to a bearing surface of the wheel, the planetary gear is mounted eccentrically on a supporting base, and the annulus is held in a non-rotating relationship with the supporting base.

* * * * *